United States Patent
Narabu et al.

(10) Patent No.: US 8,084,398 B2
(45) Date of Patent: Dec. 27, 2011

(54) BENZOYLPYRAZOLES AND HERBICIDE

(75) Inventors: Shinichi Narabu, Ibaraki (JP); Yasushi Yoneta, Saitama (JP); Akihiko Yanagi, Tochigi (JP); Shinichi Shirakura, Tochigi (JP); Seiji Ukawa, Tochigi Pref (JP); Teruyuki Ichihara, Tochigi (JP); Shin Nakamura, Tochigi (JP); Martin Hills, Idstein (DE); Heinz Kehne, Hofheim (DE); Jan Dittgen, Frankfurt (DE); Dieter Feucht, Eschborn (DE); Christopher Rosinger, Hofheim (DE)

(73) Assignee: Bayer Cropscience AG, Monheim (DE)

( * ) Notice: Subject to any disclaimer, the term of this patent is extended or adjusted under 35 U.S.C. 154(b) by 265 days.

(21) Appl. No.: 12/444,554

(22) PCT Filed: Oct. 2, 2007

(86) PCT No.: PCT/EP2007/008551
§ 371 (c)(1),
(2), (4) Date: Jul. 30, 2009

(87) PCT Pub. No.: WO2008/043456
PCT Pub. Date: Apr. 17, 2008

(65) Prior Publication Data
US 2010/0094023 A1    Apr. 15, 2010

(30) Foreign Application Priority Data
Oct. 13, 2006   (JP) ................. 2006-279533

(51) Int. Cl.
*A01N 43/713* (2006.01)
*C07D 231/20* (2006.01)
*C07D 403/12* (2006.01)
(52) U.S. Cl. .............. 504/261; 548/253; 548/369.4
(58) Field of Classification Search .................. None
See application file for complete search history.

(56) References Cited

U.S. PATENT DOCUMENTS

| | | | |
|---|---|---|---|
| 5,468,722 | A | 11/1995 | Shibiata et al. |
| 6,624,121 | B1 | 9/2003 | Yanagi et al. |
| 6,864,219 | B2 | 3/2005 | Schallner et al. |
| 2005/0090398 | A1 | 4/2005 | Yanagi et al. |

FOREIGN PATENT DOCUMENTS

| | | |
|---|---|---|
| DE | 10039723 | 7/2001 |
| EP | 0369803 | 5/1990 |
| JP | 61257974 | 11/1986 |
| JP | 6247891 | 9/1994 |
| JP | 7206808 | 8/1995 |
| JP | 10109976 | 4/1998 |

OTHER PUBLICATIONS

International Search Report; dated Dec. 6, 2007 (3 pages).
International Preliminary Report on Patentability (IPER) PCT/EP2007/008551, dated Sep. 11, 2008; (5 pages).

*Primary Examiner* — Kamal Saeed
(74) *Attorney, Agent, or Firm* — Baker Donelson Bearman, Caldwell & Berkowitz, PC

(57) ABSTRACT

Benzoylpyrazoles represented by the following formula (I), and use thereof as herbicides.

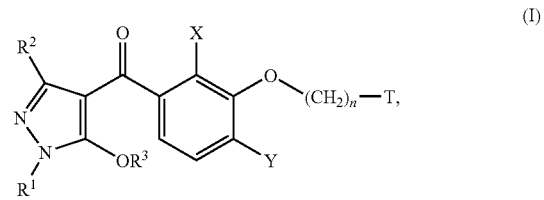

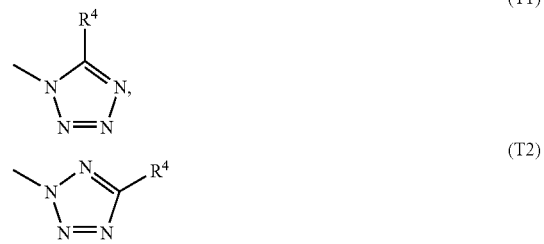

$R^1$ represents alkyl;
$R^2$ represents alkyl or cycloalkyl;
$R^3$ represents hydrogen, alkyl, alkenyl, alkynyl, aralkyl, alkylsulfonyl, optionally substituted phenylsulfonyl, acyl or acylalkyl;
X represents halogen or alkyl;
Y represents halogen; n represents 2 or 3, and
T represents the above group T1 or T2, wherein $R^4$ represents hydrogen, alkyl, alkoxy or alkylthio.

8 Claims, No Drawings

BENZOYLPYRAZOLES AND HERBICIDE

CROSS REFERENCE TO RELATED APPLICATIONS

This application is a §371 National Stage Application of PCT/EP2007/008551 filed Oct. 2, 2007 which claims priority to Japanese Application 2006-279533 filed Oct. 13, 2006.

BACKGROUND OF THE INVENTION

1. Field of the Invention

The present invention relates to novel benzoylpyrazoles, their use as herbicides, to process for their preparation and to their novel intermediates.

2. Description of Related Art

It has already been known that a certain kind of benzoylpyrazoles exhibits an action as herbicides (e.g., PCT International Publications WO03/66607, WO01/10850 and WO01/53275).

SUMMARY OF THE INVENTION

However, compounds disclosed in the above publications are not satisfactory enough from the viewpoints of efficacy as herbicides and/or their safety.

The present inventors have intensively studied to create novel compounds having higher efficacy as herbicides and being safer. As a result, the present inventors have found novel benzoylpyrazoles represented by the formula set forth below which exhibit superior herbicidal activity and safety against crops.

Benzoylpyrazoles represented by the formula (I):

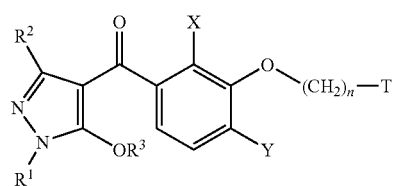

(I)

wherein
$R^1$ represents alkyl;
$R^2$ represents alkyl or cycloalkyl;
$R^3$ represents hydrogen, alkyl, alkenyl, alkynyl, aralkyl, alkylsulfonyl, optionally substituted phenylsulfonyl, acyl or acylalkyl;
X represents halogen or alkyl;
Y represents halogen;
n represents 2 or 3, and
T represents a group T1:

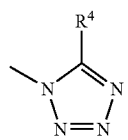

(T1)

or a group T2:

(T2)

wherein $R^4$ represents hydrogen, alkyl, alkoxy or alkylthio.

The compounds of the above formula (I) of the present invention can be synthesized, for example, by either of the preparation process (a) or (b) set forth below. Preparation process (a): compounds of formula (I) wherein $R^3$ represents hydrogen:

A process of rearranging compounds represented by the formula (II):

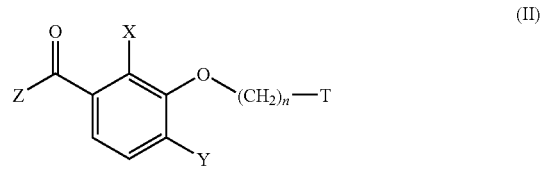

(II)

wherein X, Y, n and T are as defined above and Z represents a group:

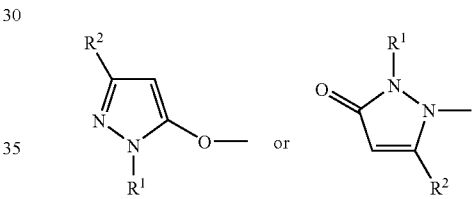

wherein $R^1$ and $R^2$ are as defined above.

Preparation process (b): compounds of formula (I) wherein $R^3$ represents alkyl, alkenyl, alkynyl, aralkyl, alkylsulfonyl, optionally substituted phenylsulfonyl, acyl or acylalkyl:

A process of reacting compounds represented by the formula (Ia):

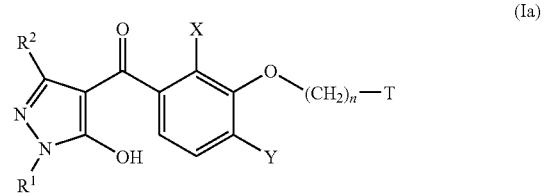

(Ia)

wherein $R^1$, $R^2$, X, Y, n and T are as defined above, with compounds represented by the formula (III):

(III)

wherein
$R^3$ is as defined above and
L represents halogen.

The benzoylpyrazoles of the formula (I) provided by the present invention have a more potent herbicidal activity than the compounds described in the above prior art documents while exhibiting extremely superior efficacy as selective herbicides without substantially no phytotoxity to crops. Particularly, the benzoylpyrazoles of the formula (I) exhibit extremely superior efficacy as herbicides for Leguminous dry field crops such as soy beans and Poaceae dry field crops such as wheat, barley, oats and corn.

Accordingly, the benzoylpyrazoles of the formula (I) of the present invention are particularly useful as herbicides for dry field.

BEST MODE FOR CARRYING OUT THE INVENTION

In the present specification, the term "halogen" means fluorine, chlorine, bromine or iodine, and preferably chlorine and bromine.

The term "alkyl" may be those of a linear or branched chain, and means for example $C_{1-6}$ alkyl. Specifically, examples of "alkyl" include methyl, ethyl, n- or iso-propyl, n-, iso-, sec- or tert-butyl, n-, iso-, neo- or tert-pentyl, n- or iso-hexyl and the like.

Examples of "cycloalkyl" include cyclopropyl, cyclobutyl, cyclopentyl, cyclohexyl, cycloheptyl and the like.

Examples of "alkenyl" include allyl, 1-methylallyl, 1,1-dimethylallyl, 2-butenyl, 2-pentenyl, 2-hexenyl, 2-heptenyl and the like.

Examples of "alkynyl" include ethynyl, 2-propynyl, 1-methyl-2-propynyl, 1,1-dimethyl-2-propynyl, 2-butynyl, 2-pentynyl, 2-hexynyl, 2-heptynyl and the like.

The term "aralkyl" means, for example, an arylalkyl group the alkyl moiety of which has the above meaning, and the "aryl" means, for example, phenyl, naphthyl and the like, and specifically, benzyl.

The term "alkoxy" means, for example, an alkyl-O— group the alkyl moiety of which has the above meaning, and can be, for example, $C_{1-6}$ alkoxy. Specifically, examples of "alkoxy" include methoxy, ethoxy, n- or iso-propoxy, n-, iso-, sec- or tert-butoxy, n-pentyloxy, n-hexyloxy and the like.

The term "alkylthio" means an alkyl-S— group the alkyl moiety of which has the above meaning, and can be, for example, $C_{1-6}$ alkylthio. Specifically, examples of "alkylthio" include methylthio, ethylthio, n- or iso-propylthio, n-, iso-, sec- or tert-butylthio, n-penthylthio, n-hexylthio and the like.

The term "alkylsulfonyl" means an alkyl-$SO_2$— group the alkyl moiety of which has the above meaning, and can be, for example, $C_{1-6}$ alkylsulfonyl. Specifically, examples of "alkylsulfonyl" include methylsulfonyl, ethylsulfonyl, n- or iso-propylsulfonyl, n-, iso-, sec- or tert-butylsulfonyl, n-pentylsulfonyl, n-hexylsulfonyl and the like.

"Acyl" is an acyl group derived from aliphatic saturated monocarboxylic acid, or aliphatic or aromatic hydrocarbon ring carboxylic acid, and means for example, a $C_{1-6}$ alkyl-CO— group the alkyl moiety of which has the above meaning, or an aryl-CO— group the aryl moiety of which is as defined above. Specifically, examples of "acyl" include acetyl, propionyl, butyryl, isobutyryl, valeryl, isovaleryl, pivaloyl, n-pentylcarbonyl, n-hexylcarbonyl, benzoyl and the like.

"Acylalkyl" is an acylalkyl group the acyl and alkyl moieties of which have the above meaning, and means for example, a benzoyl-$C_{1-6}$ alkyl group, and specifically, includes phenacyl and the like.

A preferable group of compounds of the invention includes those of the formula (I), wherein $R^1$ represents $C_{1-6}$ alkyl;

$R^2$ represents $C_{1-6}$ alkyl or $C_{3-7}$ cycloalkyl;

$R^3$ represents hydrogen, $C_{1-6}$ alkyl, $C_{3-7}$ alkenyl, $C_{3-7}$ alkynyl, $C_{7-12}$ aralkyl, $C_{1-6}$ alkylsulfonyl, optionally $C_{1-6}$ alkyl-substituted phenylsulfonyl, $C_{1-6}$ alkyl-carbonyl, benzoyl or benzoyl-$C_{1-6}$ alkyl;

X represents halogen or $C_{1-6}$ alkyl;

Y represents halogen;

n represents 2 or 3; and

T represents a group represented by

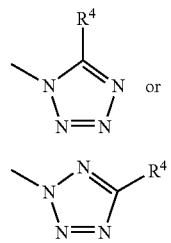

(T1)

(T2)

wherein $R^4$ represents hydrogen, $C_{1-6}$ alkyl, $C_{1-6}$ alkoxy or $C_{1-6}$ alkylthio.

A more preferable group of the compounds of the invention includes those of the formula (I), wherein $R^1$ represents methyl or ethyl;

$R^2$ represents methyl, ethyl or cyclopropyl;

$R^3$ represents hydrogen, methyl, allyl, propargyl, benzyl, methanesulfonyl, n-propanesulfonyl, optionally methyl-substituted phenylsulfonyl, acetyl, benzoyl or phenacyl;

X represents chlorine, bromine or methyl;

Y represents chlorine or bromine;

n represents 2 or 3; and

T represents a group represented by

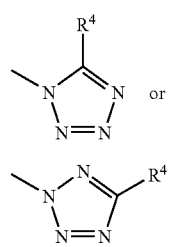

(T1)

(T2)

wherein $R^4$ represents hydrogen, methyl, ethyl, methoxy or methylthio.

Using, for example, 5-{2,4-dichloro-3-[2-(1H-tetrazol-1-yl)ethyloxy]benzoyloxy}-1,3-dimethylpyrazole, acetone cyanohydrine as a cyanide, and triethylamine as a base, the preparation process (a) mentioned above is represented by the following reaction scheme:

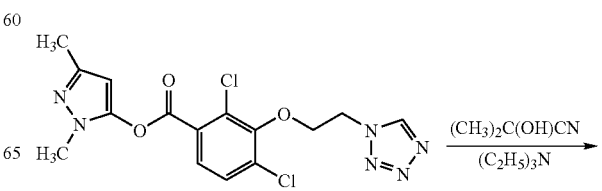

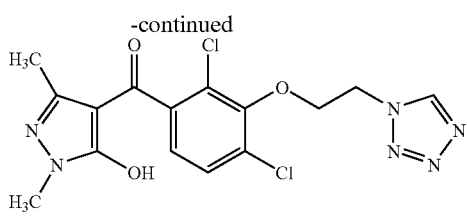

Using, for example, 4-{2,4-dichloro-3-[2-(1H-tetrazol-1-yl)ethyloxy]benzoyl}-1,3-dimethyl-5-hydroxypyrazole, benzyl bromide and potassium carbonate as an acid coupling agent, the preparation process (b) mentioned above is represented by the following reaction scheme:

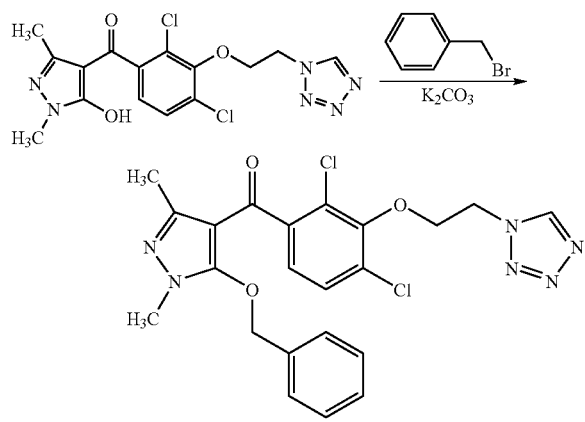

The compounds of the formula (I) of the present invention can exist as tautomers when $R^3$ represents hydrogen, as shown by the following formulae (Ia), (Ib) and (Ic).

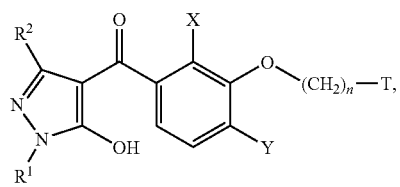
(Ia)

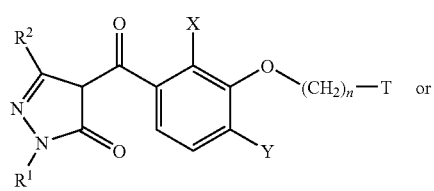
(Ib)

or

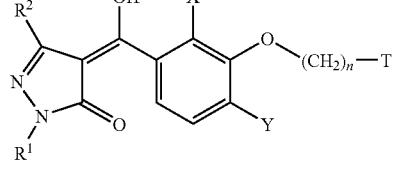
(Ic)

The compounds of the formula (II) used as raw materials in the above preparation process (a) are novel compounds not described in prior literatures. They may be prepared in accordance with the processes described in, for example, Japanese Patent KOKAI Publication No. 2-173 (hereinafter "Japanese Patent KOKAI Publication No." is referred to as "JP-A-"), WO93/18031 and the like. Namely, they can be prepared by reacting compounds represented by the formula (IV):

$$Z—H \quad (IV)$$

wherein Z is as defined above with compounds represented by the formula (V):

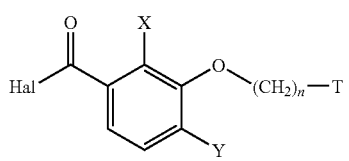
(V)

wherein X, Y, n and T are as defined above and Hal represents halogen, preferably chlorine or bromine, in the presence of a suitable acid coupling agent, for example, triethylamine in a suitable diluent, for example, dichloromethane.

The compounds represented by the above formula (IV) per se are known and can be prepared according to the processes described in literatures, for example, JP-A-61-257974, JP-A-10-109976 and the like.

A part of the compounds represented by the above formula (V) are novel compounds not described in prior literatures and can be prepared in accordance with the processes described in literatures, for example, JP-A-2-173, WO93/18031, WO03/66607 and the like. Namely, they can be prepared by reacting compounds represented by the formula (VI):

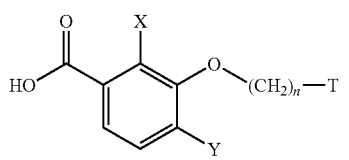
(VI)

wherein X, Y, n and T are as defined above with halogenating agents such as, for example, phosphorus oxychloride, phosphorus oxybromide, phosphorus trichloride, phosphorus tribromide, phosgene, oxalyl dichloride, thionyl chloride and thionyl bromide.

A part of the compounds represented by the above formula (VI) are novel compounds not described in prior literatures and can be prepared in accordance with the processes described in literatures, for example, JP-A-2-173, WO03/66607 and the like. Namely, they can be prepared by hydrolyzing compounds represented by the formula (VII):

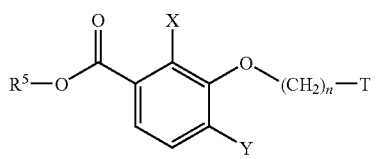
(VII)

wherein X, Y, n and T are as defined above and $R^5$ represents $C_{1-4}$ alkyl, preferably methyl or ethyl in the presence of a suitable base, for example, sodium hydroxide in a diluent, for example, aqueous dioxane.

A part of the compounds represented by the above formula (VII) are novel compounds not described in prior literatures and can be prepared in accordance with the processes described in literatures, for example, German Patent No. 10039723, WO03/66607 and the like. Namely, they can be prepared by reacting compounds represented by the formula (VIII):

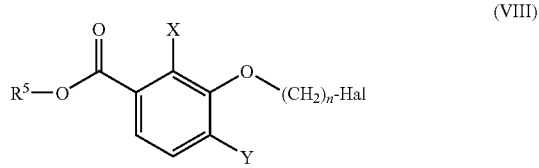

(VIII)

wherein X, Y and n and are as defined above and $R^5$ represents $C_{1-4}$ alkyl, preferably methyl or ethyl, and Hal represents halogen, preferably chlorine or bromine with the compounds represented by the formula (IX)

(IX)

wherein T is as defined above, in the presence of a suitable condensing agent, for example, potassium carbonate in a suitable diluent, for example, N,N-dimethylformamide.

The compounds represented by the above formula (VIII) per se are known and can be easily prepared by the processes described in, for example, JP-A-6-247891, JP-A-7-206808, European Patent No. 369803 and the like.

The compounds represented by the above formula (IX) per se are known and can be easily prepared by the processes described in, for example, Journal of the American Chemical Society, Vol. 80, p. 3908-3911 (1958), Journal of Organic Chemistry, Vol. 22, p. 1142-1145 (1957), Journal of Organic Chemistry, Vol. 56, p. 2395-2400 (1991), JP-A-9-309883 and the like.

Representative examples of the compounds of the formula (II) used as raw materials in the above preparation process (a) include those described below.
5-{2,4-Dichloro-3-[2-(1H-tetrazol-1-yl)ethyloxy]-benzoyloxy}-1,3-dimethylpyrazole,
5-{2,4-dichloro-3-[2-(2H-tetrazol-2-yl)ethyloxy]-benzoyloxy}-1,3-dimethylpyrazole,
5-{2,4-dichloro-3-[2-(1H-tetrazol-1-yl)ethyloxy]-benzoyloxy}-1-methyl-3-cyclopropylpyrazole,
5-{2-methyl-3-[2-(5-methyl-1H-tetrazol-1-yl)-ethyloxy]-4-bromobenzoyloxy}-1,3-dimethylpyrazole,
5-{2-methyl-3-[2-(5-methyl-2H-tetrazol-2-yl)-ethyloxy]-4-bromobenzoyloxy}-1,3-dimethylpyrazole,
5-{2-methyl-3-[2-(5-methyl-1H-tetrazol-1-yl)-ethyloxy]-4-chlorobenzoyloxy}-1,3-dimethylpyrazole,
5-{2-methyl-3-[2-(5-ethyl-1H-tetrazol-1-yl)ethyloxy]-4-bromobenzoyloxy}-1,3-dimethylpyrazole,
5-{2,4-dichloro-3-[2-(5-methylthio-1H-tetrazol-1-yl)ethyloxy]benzoyloxy}-1,3-dimethylpyrazole,
5-{2-methyl-3-[2-(5-methoxy-1H-tetrazol-1-yl)-ethyloxy]-4-bromobenzoyloxy}-1,3-dimethylpyrazole,
5-{2-methyl-3-[2-(2H-tetrazol-2-yl)ethyloxy]-4-bromobenzoyloxy}-1-methyl-3-ethylpyrazole,
5-{2,4-dichloro-3-[3-(1H-tetrazol-1-yl)propyloxy]-benzoyloxy}-1,3-dimethylpyrazole,
1-{2,4-dichloro-3-[2-(1H-tetrazol-1-yl)ethyloxy]-benzoyl}-2,5-dimethyl-1,2-dihydro-3H-pyrazol-3-one, and etc.

Representative examples of the compounds of the formula (IV) used as raw materials in the preparation of the compounds of the above formula (II) include those described below.
1,3-Dimethyl-5-hydroxypyrazole,
1-methyl-3-ethyl-5-hydroxypyrazole,
1-methyl-3-cyclopropyl-5-hydroxypyrazole,
1-ethyl-3-methyl-5-hydroxypyrazole,
1-ethyl-3-cyclopropyl-5-hydroxypyrazole, and etc.

Representative examples of the compounds of the formula (V) used as raw materials in the preparation of the compounds of the above formula (II) include those described below.
2,4-Dichloro-3-[2-(1H-tetrazol-1-yl)ethyloxy]benzoyl chloride,
2,4-dichloro-3-[2-(2H-tetrazol-2-yl)ethyloxy]benzoyl chloride,
2-methyl-3-[2-(5-methyl-1H-tetrazol-1-yl)ethyloxy]-4-bromobenzoyl chloride,
2-methyl-3-[2-(5-methyl-2H-tetrazol-2-yl)ethyloxy]-4-bromobenzoyl chloride,
2-methyl-3-[2-(1H-tetrazol-1-yl)ethyloxy]-4-chlorobenzoyl chloride,
2,4-dichloro-3-[2-(5-thiomethyl-1H-tetrazol-1-yl)ethyloxy]benzoyl chloride,
2-methyl-3-[2-(5-methoxy-1H-tetrazol-1-yl)ethyloxy]-4-bromobenzoyl chloride,
2,4-dichloro-3-[3-(1H-tetrazol-1-yl)propyloxy]benzoyl chloride, and etc.

Representative examples of the compounds of the formula (VI) used as raw materials in the preparation of the compounds of the above formula (V) include those described below.
2,4-Dichloro-3-[2-(1H-tetrazol-1-yl)ethyloxy]benzoic acid,
2,4-dichloro-3-[2-(2H-tetrazol-2-yl)ethyloxy]benzoic acid,
2-methyl-3-[2-(5-methyl-1H-tetrazol-1-yl)ethyloxy]-4-bromobenzoic acid,
2-methyl-3-[2-(5-methyl-2H-tetrazol-2-yl)ethyloxy]-4-bromobenzoic acid,
2-methyl-3-[2-(1H-tetrazol-1-yl)ethyloxy]-4-chlorobenzoic acid,
2,4-dichloro-3-[2-(5-thiomethyl-1H-tetrazol-1-yl)-ethyloxy]benzoic acid,
2-methyl-3-[2-(5-methoxy-1H-tetrazol-1-yl)ethyloxy]-4-bromobenzoic acid,
2,4-dichloro-3-[3-(1H-tetrazol-1-yl)propyloxy]benzoic acid, and etc.

Representative examples of the compounds of the formula (VII) used as raw materials in the preparation of the compounds of the above formula (VI) include those described below.
Ethyl 2,4-dichloro-3-[2-(1H-tetrazol-1-yl)ethyloxy]-benzoate,
ethyl 2,4-dichloro-3-[2-(2H-tetrazol-2-yl)ethyloxy]-benzoate,
ethyl 2-methyl-3-[2-(5-methyl-1H-tetrazol-1-yl)-ethyloxy]-4-bromobenzoate,
ethyl 2-methyl-3-[2-(5-methyl-2H-tetrazol-2-yl)-ethyloxy]-4-bromobenzoate,
methyl 2-methyl-3-[2-(1H-tetrazol-1-yl)ethyloxy]-4-chlorobenzoate,
ethyl 2,4-dichloro-3-[2-(5-thiomethyl-1H-tetrazol-1-yl) ethyloxy]benzoate,
ethyl 2-methyl-3-[2-(5-methoxy-1H-tetrazol-1-yl)-ethyloxy]-4-bromobenzoate,
ethyl 2,4-dichloro-3-[3-(1H-tetrazol-1-yl)-propyloxy]benzoate, and etc.

Representative examples of the compounds of the formula (VIII) used as raw materials in the preparation of the compounds of the above formula (VII) include those described below.
Ethyl 2,4-dichloro-3-(2-bromoethoxy)benzoate,
ethyl 2-methyl-3-(2-bromoethoxy)-4-bromobenzoate,
methyl 2-methyl-3-(2-bromoethoxy)-4-chlorobenzoate,
ethyl 2,4-dichloro-3-(2-chloroethoxy)benzoate,
ethyl 2,4-dichloro-3-(2-iodoethoxy)benzoate, ethyl 2,4-dichloro-3-(3-bromopropyloxy)benzoate, and etc.

Representative examples of the compounds of the formula (IX) used as raw materials in the preparation of the compounds of the above formula (VII) include those described below.

1H-tetrazole,
5-methyl-1H-tetrazole,
5-ethyl-1H-tetrazole,
5-methylthio-1H-tetrazole,
5-methoxy-1H-tetrazole, and etc.

The compounds of the formula (Ia), which are raw materials in the above preparation process (b), constitute a part of the compounds represented by the formula (I) of the present invention and can be easily prepared in accordance with the above preparation process (a).

Representative examples of the compounds of the formula (Ia) used as raw materials in the preparation process (b) include those described below which are encompassed by the formula (I).

4-{2,4-Dichloro-3-[2-(1H-tetrazol-1-yl)ethyloxy]-benzoyl}-1,3-dimethyl-5-hydroxypyrazole,
4-{2,4-dichloro-3-[2-(2H-tetrazol-2-yl)ethyloxy]-benzoyl}-1,3-dimethyl-5-hydroxypyrazole,
4-{2,4-dichloro-3-[2-(1H-tetrazol-1-yl)ethyloxy]-benzoyl}-1-methyl-3-cyclopropyl-5-hydroxypyrazole,
4-{2-methyl-3-[2-(1H-tetrazol-1-yl)ethyloxy]-4-bromobenzoyl}-1,3-dimethyl-5-hydroxypyrazole,
4-{2-methyl-3-[2-(2H-tetrazol-2-yl)ethyloxy]-4-bromobenzoyl}-1,3-dimethyl-5-hydroxypyrazole,
4-{2-methyl-3-[2-(1H-tetrazol-1-yl)ethyloxy]-4-chlorobenzoyl}-1,3-dimethyl-5-hydroxypyrazole, and etc.

The compounds of the formula (III), which are raw materials in the above preparation process (b), are halogenated alkyl, halogenated alkenyl, halogenated alkynyl, halogenated aralkyl, halogenated acyl, halogenated sulfonyl and acylalkyl halide that are well known themselves in the field of organic chemistry, and those described below can be exemplified.

Methyl iodide,
propargyl bromide,
benzyl bromide,
n-propane sulfonyl chloride,
4-methylbenzene sulfonyl chloride,
acetyl chloride,
phenacyl bromide and etc.

The reaction of the above preparation process (a) can be carried out in a suitable diluent and examples thereof that may be used during the process include aliphatic, alicyclic and aromatic hydrocarbons (which may be optionally chlorinated), for example, pentane, hexane, cyclohexane, petroleum ether, ligroin, toluene, xylene, dichloromethane, 1,2-dichloroethane and etc;

ethers such as for example, ethyl ether, methyl ethyl ether, isopropyl ether, butyl ether, dioxane, dimethoxyethane (DME), tetrahydrofuran (THF) and diethylene glycol dimethyl ether (DGM);

ketones such as for example, acetone, methyl ethyl ketone (MEK), methyl isopropyl ketone and methyl isobutyl ketone (MIBK);

nitriles such as for example, acetonitrile and propionitrile;
alcohols such as for example, methanol, ethanol and isopropanaol;
esters such as for example, ethyl acetate, amyl acetate;
acid amides such as for example, dimethylformamide (DMF), dimethylacetamide (DMA), N-methylpyrrolidone and 1,3-dimethyl-2-imidazolidinone;

sulfones and sulfoxifdes such as dimethylsulfoxide (DMSO) and sulfolane; and bases such as for example, pyridine.

The preparation process (a) can be carried out in the presence of a base. Examples of the base includes, from inorganic bases, carbonates and bicarbonates of alkali metal and alkali earth metal such as for example, sodium bicarbonate, potassium bicarbonate, sodium carbonate and potassium carbonate; and from organic bases, tertiary amines, dialkylaminoanilines and pyridines such as for example, triethylamine, 1,1,4,4-tetramethylethylenediamine (TMEDA), N,N-dimethylaniline, N,N-diethylaniline, pyridine, 4-dimethylaminopyridine (DMAP), 1,4-diazabicyclo[2,2,2]octane (DABCO) and 1,8-diazabicyclo[5,4,0]undec-7-ene (DBU).

The preparation process (a) can be carried out in the presence of cyanide. Examples of the catalysts include sodium cyanide, potassium cyanide, acetone cyanohydrin, hydrogen cyanide and the like.

When the above preparation process (a) is carried out in the presence of cyanide, it can also be carried out by a method using phase-transfer catalysts. Examples of a diluent that may be used during the preparation include aliphatic, alicyclic and aromatic hydrocarbons (which may be optionally chlorinated), for example, pentane, hexane, cyclohexane, petroleum ether, ligroin, toluene, xylene, dichloromethane and the like;

ethers such as for example, ethyl ether, methyl ethyl ether, isopropyl ether, butyl ether, dioxane, dimethoxyethane (DME), tetrahydrofuran (THF) and diethylene glycol dimethyl ether (DGM);

nitriles such as for example, acetonitrile and propionitrile.

Examples of the phase-transfer catalysts include crown ethers such as for example, dibenzo-18-crown-6, dicyclohexyl-18-crown-6, 18-crown-6 and 15-crown-5.

The preparation process (a) can be carried out within a substantially wide range of temperatures.

In general, the suitable range of temperatures is between about 5° C. to about 200° C. and preferably about 25° C. to about 130° C. Further, the reaction is conducted desirably under normal pressure, but it can also be operated under elevated pressure or reduced pressure.

In carrying out the preparation process (a), 0.5 to 2 mol of potassium carbonate are reacted per mole of the compound of the formula (II) in a diluent, for example, dioxane to give the objective compound of the formula (I).

When the preparation process (a) is carried out in the presence of cyanide, it can be carried out within a substantially wide range of temperatures.

In general, the suitable range of temperatures is between about −10° C. to about 80° C. and preferably about 5° C. to about 40° C. Further, the reaction is conducted desirably under normal pressure, but it can also be operated under elevated pressure or reduced pressure.

In carrying out the preparation process (a) in the presence of cyanide, 1 to 4 mol of triethylamine is reacted per mole of the compound of the formula (II) in the presence of 0.01 to 0.5 mol of acetone cyanohydrin in a diluent, for example, acetonitrile to give the objective compound of the formula (I).

In carrying out the preparation process (a), the compounds of the formula (I) can be obtained by starting from the compounds of the formula (VI) and continuously carrying out one pot reaction without isolating the compounds of the formula (V) and those of the formula (II).

The reaction of the above preparation process (b) can be carried out in a suitable diluent and examples thereof that may be used during the process include water;

aliphatic, alicyclic and aromatic hydrocarbons (which may be optionally chlorinated), for example, pentane, hexane, cyclohexane, petroleum ether, ligroin, benzene, toluene, xylene, dichloromethane, chloroform, carbon tetrachloride, 1,2-dichloroethane, chlorobenzene, dichlorobenzene and the like;

ethers such as for example, ethyl ether, methyl ethyl ether, isopropyl ether, butyl ether, dioxane, dimethoxyethane (DME), tetrahydrofuran (THF) and diethylene glycol dimethyl ether (DGM);

ketones such as for example, acetone, methyl ethyl ketone (MEK), methyl isopropyl ketone and methyl isobutyl ketone (MIBK);

nitriles such as for example, acetonitrile, propionitrile and acrylonitrile;

esters such as for example, ethyl acetate and amyl acetate;

acid amides such as for example, dimethylformamide (DMF), dimethylacetamide (DMA), N-methylpyrrolidone and 1,3-dimethyl-2-imidazolidinone, hexamethylphosphoric triamide (HMPA);

sulfones and sulfoxifdes such as for example, dimethylsulfoxide (DMSO) and sulfolane; and bases such as for example, pyridine.

The preparation process (b) can be carried out in the presence of acid coupling agents. The acid coupling agents include, from inorganic bases, hydrides, hydroxides, carbonates and bicarbonates of alkali metal and alkali earth metal such as for example, sodium hydride, lithium hydride, sodium bicarbonate, potassium bicarbonate, sodium carbonate, potassium carbonate, lithium hydroxide, sodium hydroxide, potassium hydroxide and calcium hydroxide; and from organic bases, alkolates, tertiary amines, dialkylaminoanilines and pyridines such as for example, triethylamine, 1,1,4,4-tetramethylethylenediamine (TMEDA), N,N-dimethylaniline, N,N-diethylaniline, pyridine, 4-dimethylaminopyridine (DMAP), 1,4-diazabicyclo[2,2,2]octane (DABCO) and 1,8-diazabicyclo[5,4,0]undec-7-ene (DBU).

The preparation process (b) can also be carried out by a process of using phase-transfer catalysts. Examples of a diluent that may be used during the preparation include water;

aliphatic, alicyclic and aromatic hydrocarbons (which may be optionally chlorinated), for example, pentane, hexane, cyclohexane, petroleum ether, ligroin, benzene, toluene, xylene, dichloromethane, chlorobenzene, dichlorobenzene and the like;

ethers such as for example, ethyl ether, methyl ethyl ether, isopropyl ether, butyl ether, dioxane, dimethoxyethane (DME), tetrahydrofuran (THF) and diethylene glycol dimethyl ether (DGM);

nitriles such as for example, acetonitrile, propionitrile and acrylonitrile; and the like.

The examples of the phase-transfer catalysts include quaternary ions such as for example, tetramethylammonium bromide,
tetrapropylammonium bromide,
tetrabutylammonium bromide,
tetrabutylammonium bissulfate,
tetrabutylammonium iodide,
trioctylmethylammonium chloride,
benzyltriethylammonium bromide,
butylpyridinium bromide,
heptylpyridinium bromide and
benzyltriethylammonium chloride;

crown ethers such as for example, dibenzo-18-crown-6, dicyclohexyl-18-crown-6 and 18-crown-6;

cryptands such as for example, [2.2.2]-cryptate, [2.1.1]-cryptate, [2.2.1]-cryptate, [2.2.B]-cryptate, [2O2O2S]-cryptate and [3.2.2]-cryptate.

The preparation process (b) can be carried out within a substantially wide range of temperatures.

In general, the suitable range of temperatures is between about −20° C. to about 140° C. and preferably about 0° C. to about 100° C. Further, the reaction is conducted desirably under normal pressure, but it can also be operated under elevated pressure or reduced pressure.

In carrying out the preparation process (b), 1 mol to 5 mol of the compound of the formula (III) is reacted per mole of the compound of the formula (Ia) in the presence of potassium carbonate in a diluent, for example, DMF to give the objective compound.

The active compounds of the formula (I) according to the present invention exhibit superior herbicidal activity for various weeds as shown in Biological Test Examples to be described later and can be used as herbicides. In the present specification weeds mean, in the broadest sense, all plants that grow in locations where they are undesired. The compounds of the present invention act as selective herbicides depending on the application concentration. The active compounds according to the present invention can be used, for example, between the following weeds and cultures.

From the genus of dicotyledonous weeds: *Sinapis, Capsella, Leipidium, Galium, Stellaria, Chenopodium, Kochia, Urtica, Senecio, Amaranthus, Portulaca, Xanthium, Ipomoea, Polygonum, Ambrosia, Cirsium, Sonchus, Solanum, Rorippa, Lamium, Veronica, Datura, Viola, Galeopsis, Papaver, Centaurea, Galinsoga, Rotala, Lindernia, Sesbania, Trifolium, Abutilon, Lamium, Matricaria, Artemisia, Sesbania, Pharbitis, Amaranthus*, and the like.

From the genus of dicotyledonous cultures: *Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cucurbita*, and the like.

From the genus of monocotyledonous weeds: *Echinochlona, Setaria, Panicum, Digitaria, Phleum, Poa, Festuca, Eleusine, Lolium, Bromus, Avena, Cyperus, Sorghum, Agropyron, Monochoria, Fimbristylis, Sagittaria, Eleocharis, Scirpus, Paspalum, Ischaemum, Agrostis, Alopecurus, Cynodon, Commelina, Brachiaria, Leptochloa*, and the like.

From the genus of monocotyledonous cultures: *Oryza, Zea, Triticum, Hordeum, Avena, Secale, Sorghum, Panicum, Saccharum, Ananas, Asparagus, Allium*, and the like.

However, the use of the active compounds of the formula (I) of the present invention is not limited to the above species of weeds but can also be applied to other species of weeds similarly.

The use of the active compounds of the present invention is not limited to the above plants but can also be applied to other plants similarly. Further, the active compounds of the present invention can non-selectively control weeds and can be used, for example, in industrial areas such as factories, railway tracks, roads, plantations, non plantation and the like, depending on the application concentration. Similarly, the compounds can also be used for controlling weeds in perennial plant cultivation such as, for example, afforestations, decorative tree plantings, orchards, vineyards, citrus groves, nut orchards, banana plantations, coffee plantations, tee plantations, rubber plantations, oil palm plantations, cocoa plantations, soft fruit plantings and hopfields. The compounds of the present invention can also be applied for selectively controlling weeds in annual plant cultivation.

The active compounds of the present invention can be made into the customary formulations for actual use. Examples of the formulation forms include solutions, wettable powders, emulsions, suspensions, dusts, water-dispersible granules, tablets, granules, suspended emulsifiable concentrates, microcapsules in a polymer substance and etc.

These formulations can be produced by known methods per se. For example, they can be prepared by mixing the active compounds with extenders, namely, liquid or solid diluents or carriers and, optionally, with surfactants, namely, emulsifiers and/or dispersants and/or foam formers.

Examples of the liquid diluents or carriers include aromatic hydrocarbons (for example, xylene, toluene, alkylnaphthalene and the like), chlorinated aromatic hydrocarbons or chlorinated aliphatic hydrocarbons (for example, chlorobenzenes, ethylene chlorides, methylene chloride and the like), aliphatic hydrocarbons [for example, cyclohexane and the like, paraffins (mineral oil fractions and the like)], alcohols (for example, butanol, glycol and the like), and ethers and esters thereof, ketones (for example, acetone, methyl ethyl ketone, methyl isobutyl ketone, cyclohexanone and the like), strongly polar solvents (for example, dimethylformamide, dimethylsulfoxide and the like), water, etc. In case of using water as an extender, for example, organic solvents can be used as auxiliary solvents.

Examples of the solid diluents may include ground natural minerals (for example, kaolins, clays, talc, chalk, quartz, attapulgite, montmorillonite or diatomaceous earth) and ground synthetic minerals (for example, highly dispersed silicic acid, alumina and silicate).

Examples of the solid carriers for granules may include crushed and fractionated rocks (for example, calcite, marble, pumice, sepiolite and dolomite), synthetic granules of inorganic or organic powders, and organic materials (for example, sawdust, coconut shells, maize cobs and tobacco stalks).

Examples of the emulsifiers and/or foam formers may include nonionic and anionic emulsifiers [for example, polyoxyethylene fatty acid esters, polyoxyethylene fatty acid alcohol ethers (for example, alkylaryl polyglycol ether), alkyl sulfonates, alkyl sulfates and aryl sulfonates] and albumin hydrolysates.

The dispersants include lignin sulfite waste liquor and methylcellulose.

Binders may also be used in the formulations (powders, granules and emulsifiable concentrates). Examples of the binders may include carboxymethyl cellulose, natural or synthetic polymers (for example, gum arabic, polyvinyl alcohol and polyvinyl acetate).

Colorants may also be used. Examples of the colorants may include inorganic pigments (for example, iron oxide, titanium oxide and Prussian blue), organic colorants such as Alizarin colorants, azo colorants or metal phthalocyanine colorants, and further, trace nutrients such as salts of iron, manganese, boron, copper, cobalt, molybdenum or zinc.

The formulations can contain the active compounds of the formula (I) in a range of generally 0.1 to 95% by weight and preferably 0.5 to 90% by weight.

Further, the active compounds of the formula (I) of the present invention can be used for controlling weeds as such or in their formulation forms. The active compounds of the formula (I) of the present invention can be used also in combination with known herbicides. A mixed herbicide composition with known herbicides may be previously prepared as a final formulation form, or can be prepared by tank-mixing on occasion of application.

For example, the following herbicides shown in common names can be exemplified as specific examples of herbicides that can be used in combination with the active compounds of the formula (I) of the present invention.

Sulfonylurea type herbicides: for example, chlorsulfuron, sulfometuron methyl, chlorimuron ethyl, triasulfuron, amidosulfuron, oxasulfuron, tribenuron ethyl, prosulfuron, ethametsulfuron methyl, triflusulfuron methyl, thifensulfuron methyl, flazasulfuron, rimsulfuron, nicosulfuron, flupyrsulfuron, bensulfuron methyl, pyrazosulfuron ethyl, foramsulfuron, sulfosulfuron, cinosulfuron, azimsulfuron, metsulfuronmethyl, halosulfuron methyl, ethoxysulfuron, cyclosulfamuron and iodosulfuron;

carbamate type herbicides: for example, phenmedipham, chloropropham, asulam, bentiocarb, molinate, esprocarb, pyributicarb, dimepiperate and swep;

chloroacetanilide type herbicides: for example, propachlor, metazachlor, alachlor, acetochlor, metolachlor, butachlor, pretilachlor and thenylchlor;

diphenylether type herbicides: for example, acifluorfen, oxyfluorfen, lactofen, fomesafen, aclonifen, chlomethoxynyl, bifenox and CNP;

triazine type herbicides: for example, simazine, atrazine, propazine, cyanazine, ametryn, simetryn, dimethametryn and prometrin;

phenoxy acid or benzoic acid type herbicides: for example, 2,3,6-TBA, dicamba, quinclorac, quinmerac, clopyralid, picloram, triclopyr, fluroxypyr, fenoxaprop, diclofop methyl, fluazifop butyl, haloxyfop methyl, quizalofop ethyl, cyhalofop butyl, 2,4-PA, MCP, MCPB and phenothiol;

acid amide or urea type herbicides: for example, isoxaben, diflufenican, daiuron, linuron, fluometuron, difenoxuron, methyldymron, isoproturon, isouron, tebuthiuron, methabenzothiazuron, propanil, mefenacet, chlomeprop, naproanilide, bromobutide, daimuron, cumyluron, etobenzanid and oxadichlomefon;

organic phosphorous type herbicides: for example, glyphosate, bialaphos, glufosinate, amiprophos methyl, anilophos, bensulide, piperophos and butamiphos;

dinitroaniline type herbicides: for example, trifluralin and prodiamine;

phenolic type herbicides: for example, bromoxynil, ioxynil and dinoseb;

cyclohexanedione type herbicides: for example, alloxydim, sethoxydim, cloproxydim, clethodim, cycloxidim and tralkoxydim;

imidazolinone type herbicides: for example, imazametabenz, imazapyr, imazamethapyr, imazethapyr, imazamox and imazaquin;

bipyridium type herbicides: for example, paraquat and diquat;

carbamoyltetrazolinone type herbicides: for example, fentrazamide;

nitrile type herbicides: for example, dichlobenil; and other herbicides: for example, bentazone, tridiphane, indanofan, amitrol, carfentrazon ethyl, sulfentrazon, fenchlorazol ethyl, isoxaflutole, clomazone, maleic acid hydrazide, pyridate, chloridazon, norflurazon, pyrithiobac, bromacil, terbacil, metribuzin, oxaziclomefone, cinmethylin, flumiclorac pentyl, flumioxadin, fluthiacet methyl, azafenidin, benfuresate, oxadiazon, oxadiargyl, pentoxazone, cafenstrole, pyriminobac, bispiribac sodium, pyribenzoxim, pyriftalid, pyraflufen ethyl, benzobicyclon, dithiopyr, dalapon, and chlorthiamid.

The active compounds listed above are known herbicides described in "Pesticide Manual," 2000, published by British Crop Protect Council.

Further, the active compounds of the formula (I) of the present invention can be also mixed with safeners to reduce phytotoxicity and to provide wider weed-controlling spectrum by the mixing, thereby their application as selective herbicides can be broadened.

As examples of the safeners, the following compounds shown in common names or development codes can be mentioned;

AD-67, BAS-145138, benoxacor, cloquintocet-methyl, cyometrinil, 2,4-D, DKA-24, dichlormid, dymron, fenclorin, fenchlorazol-ethyl, flurazole, fluxofenim, furilazole, isoxadifen-ethyl), mefenpyr-diethyl), MG-191, naphthalic anhydride, oxabetrinil, PPG-1292, R-29148 and etc.

The above safeners are also described in "Pesticide Manual" 2000, published by The British Crop Protect Council.

Furthermore, the mixed herbicide compositions comprising the active compounds of the formula (I) of the present invention and the above herbicides can be further mixed with the above safeners to reduce phytotoxicity and to provide wider weed-control spectrum by the mixing, thereby their application as selective herbicides can be broadened.

Surprisingly, some of the mixed herbicide compositions of the compounds according to the present invention with known herbicides and/or safeners show synergetic effects.

In case of using the active compounds of the formula (I) of the present invention, they can be directly used as such or used in formulation forms such as formulated solutions for spraying, emulsifiable concentrates, tablets, suspensions, powders, granules or used in the use forms prepared by further dilution. The active compounds of the present invention can be applied, for example, watering, spraying, atomizing, scattering granules, and etc.

The active compounds of the formula (I) of the present invention can be used at any stage before and after germination of plants. Further, they can be also taken into the soil before sawing.

The application amount of the active compounds of the formula (I) can vary and fundamentally differs depending on the nature of the desired effect. In case of using the active compounds as herbicides, examples of the application amount, in terms of the active compounds, can be in the range of about 0.005 to about 4 kg per hectare and preferably about 0.01 to about 2 kg per hectare.

The preparation and application of the compounds of the present invention will be described more specifically by way of the following Examples, but the present invention should not be restricted to them in any way.

COMPOUND EXAMPLES

Synthesis Example 1

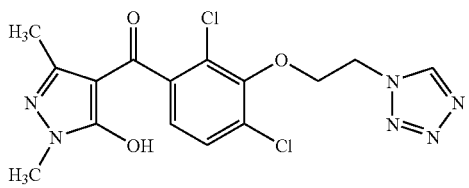

5-{2,4-Dichloro-3-[2-(1H-tetrazol-1-yl)ethyloxy]-benzoyloxy}-1,3-dimethylpyrazole (0.65 g) was dissolved in acetonitrile (10 ml), triethylamine (0.33 g) and acetone cyanohydrin (40 mg) were added thereto and the mixture was stirred at room temperature for 12 hours. The solvent was distilled off, acidified by the addition of diluted hydrochloric acid and extracted with ethyl acetate (150 ml). The organic layer was washed with saturated brine and dried with anhydrous magnesium sulfate. Ethyl acetate was distilled off to obtain objective 4-{2,4-dichloro-3-[2-(1H-tetrazol-1-yl)ethoxy]benzoyl}-1,3-dimethyl-5-hydroxy-pyrazole (0.59 g).

mp: 63-68° C.

Synthesis Example 2

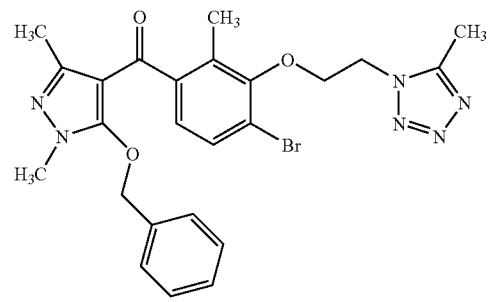

4-{2-Methyl-3-[2-(1H-tetrazol-1-yl)ethyloxy]-4-bromobenzoyl}-1,3-dimethyl-5-hydroxypyrazole (0.40 g) and potassium carbonate (0.15 g) were suspended in DMF (3 ml), benzyl bromide (0.17 g) was added thereto and the mixture was stirred at room temperature for 5 hours. After the reaction, cool water was added, the mixture was extracted with ethyl acetate (100 ml) and dried over anhydrous magnesium sulfate. The residue obtained by distilling off ethyl acetate was purified with silica gel column chromatography (elution solvent; ethyl acetate:hexane=1:1) to obtain the desired 5-{2-methyl-3-[2-(1H-tetrazol-1-yl)ethyloxy]-4-bromobenzoyloxy}-1,3-dimethyl-5-benzyloxy-pyrazole (0.37 g).

mp: 122-125° C.

The compounds obtained by operation according to the preparation processes of the compounds of the present invention exemplified in the above Synthesis Examples 1 and 2 are shown in the following Table 1 together with the compounds synthesized in Synthesis Examples 1 and 2.

In Table 1, T1 represents a group:

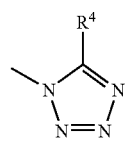

and T2 represents a group:

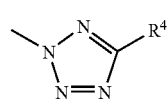

Further, Me represents methyl, Et represents ethyl, Pr-n represents n-propyl, cyclo-Pro represents cyclopropyl, OMe represents methoxy, SMe represents methylthio, $SO_2Me$ represents methanesulfonyl(methylsulfonyl), Ph represents phenyl and Ph-4-Me represents 4-methylphenyl.

TABLE 1

| Compound No. | X | Y | R¹ | R² | R³ | n | T | R⁴ | mp (° C.) or $n_D$ (° C.) |
|---|---|---|---|---|---|---|---|---|---|
| 1 | Cl | Cl | Me | Me | H | 2 | T1 | H | 63-68 |
| 2 | Cl | Cl | Me | Me | Me | 2 | T1 | H | |
| 3 | Cl | Cl | Me | Me | allyl | 2 | T1 | H | |
| 4 | Cl | Cl | Me | Me | propargyl | 2 | T1 | H | |
| 5 | Cl | Cl | Me | Me | benzyl | 2 | T1 | H | |
| 6 | Cl | Cl | Me | Me | SO₂-Me | 2 | T1 | H | |
| 7 | Cl | Cl | Me | Me | SO₂-Pr-n | 2 | T1 | H | |
| 8 | Cl | Cl | Me | Me | SO₂-Ph-4-Me | 2 | T1 | H | |
| 9 | Cl | Cl | Me | Me | CH₂C(=O)Ph | 2 | T1 | H | |
| 10 | Cl | Cl | Me | Me | C(=O)Me | 2 | T1 | H | |
| 11 | Cl | Cl | Me | Me | C(=O)Ph | 2 | T1 | H | |
| 12 | Cl | Cl | Me | Me | H | 3 | T1 | H | 53-63 |
| 13 | Cl | Cl | Me | Et | H | 2 | T1 | H | |
| 14 | Cl | Cl | Me | cyclo-Pr | H | 2 | T1 | H | 179-181 |
| 15 | Cl | Cl | Et | Me | H | 2 | T1 | H | 1.569(20) |
| 16 | Cl | Cl | Et | Et | H | 2 | T1 | H | |
| 17 | Cl | Cl | Et | cyclo-Pr | H | 2 | T1 | H | |
| 18 | Cl | Cl | Me | Me | H | 2 | T1 | Me | 142-151 |
| 19 | Cl | Cl | Me | cyclo-Pr | H | 2 | T1 | Me | 136-143 |
| 20 | Cl | Cl | Me | Me | H | 2 | T1 | Et | |
| 21 | Cl | Cl | Me | Me | H | 2 | T1 | OMe | |
| 22 | Cl | Cl | Me | Me | H | 2 | T1 | SMe | |
| 23 | Br | Br | Me | Me | H | 2 | T1 | H | 62-70 |
| 24 | Br | Br | Me | cyclo-Pr | H | 2 | T1 | H | 146-154 |
| 25 | Br | Br | Me | Me | H | 2 | T1 | Me | 55-64 |
| 26 | Br | Br | Me | cyclo-Pr | H | 2 | T1 | Me | 150-154 |
| 27 | Me | Cl | Me | Me | H | 2 | T1 | H | 135-140 |
| 28 | Me | Cl | Me | Me | Me | 2 | T1 | H | |
| 29 | Me | Cl | Me | Me | allyl | 2 | T1 | H | |
| 30 | Me | Cl | Me | Me | propargyl | 2 | T1 | H | |
| 31 | Me | Cl | Me | Me | benzyl | 2 | T1 | H | |
| 32 | Me | Cl | Me | Me | SO₂-Me | 2 | T1 | H | |
| 33 | Me | Cl | Me | Me | SO₂-Pr-n | 2 | T1 | H | |
| 34 | Me | Cl | Me | Me | SO₂-Ph-4-Me | 2 | T1 | H | |
| 35 | Me | Cl | Me | Me | CH₂C(O)Ph | 2 | T1 | H | |
| 36 | Me | Cl | Me | Me | C(=O)Me | 2 | T1 | H | |
| 37 | Me | Cl | Me | Me | C(=O)Ph | 2 | T1 | H | |
| 38 | Me | Cl | Me | Me | H | 3 | T1 | H | |
| 39 | Me | Cl | Me | Et | H | 2 | T1 | H | |
| 40 | Me | Cl | Me | cyclo-Pr | H | 2 | T1 | H | |
| 41 | Me | Cl | Et | Me | H | 2 | T1 | H | |
| 42 | Me | Cl | Et | Et | H | 2 | T1 | H | |
| 43 | Me | Cl | Et | cyclo-Pr | H | 2 | T1 | H | |
| 44 | Me | Cl | Me | Me | H | 2 | T1 | Me | 183-188 |
| 45 | Me | Cl | Me | Me | SO₂-Pr-n | 2 | T1 | Me | |
| 46 | Me | Cl | Me | Me | SO₂-Ph-4-Me | 2 | T1 | Me | |
| 47 | Me | Cl | Me | Me | CH₂C(=O)Ph | 2 | T1 | Me | |
| 48 | Me | Cl | Me | Me | H | 3 | T1 | Me | |
| 49 | Me | Cl | Me | Et | H | 2 | T1 | Me | |
| 50 | Me | Cl | Me | cyclo-Pr | H | 2 | T1 | Me | |
| 51 | Me | Cl | Et | Me | H | 2 | T1 | Me | |
| 52 | Me | Cl | Et | Et | H | 2 | T1 | Me | |
| 53 | Me | Cl | Et | cyclo-Pr | H | 2 | T1 | Me | |
| 54 | Me | Cl | Me | Me | H | 2 | T1 | Et | |
| 55 | Me | Cl | Me | Me | H | 2 | T1 | OMe | |
| 56 | Me | Cl | Me | Me | H | 2 | T1 | SMe | |
| 57 | Me | Br | Me | Me | H | 2 | T1 | H | 153-166 |
| 58 | Me | Br | Me | Me | SO₂-Pr-n | 2 | T1 | H | |
| 59 | Me | Br | Me | Me | SO₂-Ph-4-Me | 2 | T1 | H | |
| 60 | Me | Br | Me | Me | CH₂C(=O)Ph | 2 | T1 | H | |
| 61 | Me | Br | Me | Me | H | 3 | T1 | H | |
| 62 | Me | Br | Me | Et | H | 2 | T1 | H | |
| 63 | Me | Br | Me | cyclo-Pr | H | 2 | T1 | H | 151-156 |
| 64 | Me | Br | Et | Me | H | 2 | T1 | H | 108-115 |
| 65 | Me | Br | Et | Et | H | 2 | T1 | H | |
| 66 | Me | Br | Et | cyclo-Pr | H | 2 | T1 | H | |
| 67 | Me | Br | Me | Me | H | 2 | T1 | Me | 183-184 |

TABLE 1-continued

| Compound No. | X | Y | R¹ | R² | R³ | n | T | R⁴ | mp (° C.) or $n_D$ (° C.) |
|---|---|---|---|---|---|---|---|---|---|
| 68 | Me | Br | Me | Me | Me | 2 | T1 | Me | |
| 69 | Me | Br | Me | Me | allyl | 2 | T1 | Me | |
| 70 | Me | Br | Me | Me | propargyl | 2 | T1 | Me | |
| 71 | Me | Br | Me | Me | benzyl | 2 | T1 | Me | 122-125 |
| 72 | Me | Br | Me | Me | SO₂-Me | 2 | T1 | Me | |
| 73 | Me | Br | Me | Me | SO₂-Pr-n | 2 | T1 | Me | 1.5475(24) |
| 74 | Me | Br | Me | Me | SO₂-Ph-4-Me | 2 | T1 | Me | 1.5668(24) |
| 75 | Me | Br | Me | Me | CH₂C(=O)Ph | 2 | T1 | Me | 1.7445(24) |
| 76 | Me | Br | Me | Me | C(=O)Me | 2 | T1 | Me | |
| 77 | Me | Br | Me | Me | C(=O)Ph | 2 | T1 | Me | |
| 78 | Me | Br | Me | Me | H | 3 | T1 | Me | |
| 79 | Me | Br | Me | Et | H | 2 | T1 | Me | |
| 80 | Me | Br | Me | cyclo-Pr | H | 2 | T1 | Me | 1.5506(20) |
| 81 | Me | Br | Et | Me | H | 2 | T1 | Me | 166-171 |
| 82 | Me | Br | Et | Et | H | 2 | T1 | Me | |
| 83 | Me | Br | Et | cyclo-Pr | H | 2 | T1 | Me | |
| 84 | Me | Br | Me | Me | H | 2 | T1 | Et | 136-144 |
| 85 | Me | Br | Me | Me | H | 2 | T1 | OMe | |
| 86 | Me | Br | Me | Me | H | 2 | T1 | SMe | |
| 87 | Cl | Cl | Me | Me | H | 2 | T2 | H | |
| 88 | Cl | Cl | Me | Me | SO₂-Pr-n | 2 | T2 | H | |
| 89 | Cl | Cl | Me | Me | SO₂-Ph-4-Me | 2 | T2 | H | |
| 90 | Cl | Cl | Me | Me | CH₂C(=O)Ph | 2 | T2 | H | |
| 91 | Cl | Cl | Me | Et | H | 2 | T2 | H | |
| 92 | Cl | Cl | Me | cyclo-Pr | H | 2 | T2 | H | |
| 93 | Cl | Cl | Et | Me | H | 2 | T2 | H | |
| 94 | Cl | Cl | Et | Et | H | 2 | T2 | H | |
| 95 | Cl | Cl | Et | cyclo-Pr | H | 2 | T2 | H | |
| 96 | Cl | Cl | Me | Me | H | 2 | T2 | Me | 1.5807(20) |
| 97 | Cl | Cl | Me | cyclo-Pr | H | 2 | T2 | Me | 1.5852(20) |
| 98 | Cl | Cl | Me | Me | H | 2 | T2 | Et | |
| 99 | Cl | Cl | Me | Me | H | 2 | T2 | OMe | |
| 100 | Cl | Cl | Me | Me | H | 2 | T2 | SMe | |
| 101 | Br | Br | Me | Me | H | 2 | T2 | H | 1.6034(24) |
| 102 | Br | Br | Me | cyclo-Pr | H | 2 | T2 | H | 1.5986(24) |
| 103 | Br | Br | Me | Me | H | 2 | T2 | Me | 1.5905(24) |
| 104 | Br | Br | Me | cyclo-Pr | H | 2 | T2 | Me | 47-55 |
| 105 | Me | Cl | Me | Me | H | 2 | T2 | H | |
| 106 | Me | Cl | Me | Me | Me | 2 | T2 | H | |
| 107 | Me | Cl | Me | Me | allyl | 2 | T2 | H | |
| 108 | Me | Cl | Me | Me | propargyl | 2 | T2 | H | |
| 109 | Me | Cl | Me | Me | benzyl | 2 | T2 | H | |
| 110 | Me | Cl | Me | Me | SO₂-Me | 2 | T2 | H | |
| 111 | Me | Cl | Me | Me | SO₂-Pr-n | 2 | T2 | H | |
| 112 | Me | Cl | Me | Me | SO₂-Ph-4-Me | 2 | T2 | H | |
| 113 | Me | Cl | Me | Me | CH₂C(=O)Ph | 2 | T2 | H | |
| 114 | Me | Cl | Me | Me | C(=O)Me | 2 | T2 | H | |
| 115 | Me | Cl | Me | Me | C(=O)Ph | 2 | T2 | H | |
| 116 | Me | Cl | Me | Et | H | 2 | T2 | H | |
| 117 | Me | Cl | Me | cyclo-Pr | H | 2 | T2 | H | |
| 118 | Me | Cl | Et | Me | H | 2 | T2 | H | |
| 119 | Me | Cl | Et | Et | H | 2 | T2 | H | |
| 120 | Me | Cl | Et | cyclo-Pr | H | 2 | T2 | H | |
| 121 | Me | Cl | Me | Me | H | 2 | T2 | Me | 1.5524(24) |
| 122 | Me | Cl | Me | Me | SO₂-Pr-n | 2 | T2 | Me | |
| 123 | Me | Cl | Me | Me | SO₂-Ph-4-Me | 2 | T2 | Me | |
| 124 | Me | Cl | Me | Me | CH₂C(=O)Ph | 2 | T2 | Me | |
| 125 | Me | Cl | Me | Et | H | 2 | T2 | Me | |
| 126 | Me | Cl | Me | cyclo-Pr | H | 2 | T2 | Me | |
| 127 | Me | Cl | Et | Me | H | 2 | T2 | Me | |
| 128 | Me | Cl | Et | Et | H | 2 | T2 | Me | |
| 129 | Me | Cl | Et | cyclo-Pr | H | 2 | T2 | Me | |
| 130 | Me | Cl | Me | Me | H | 2 | T2 | Et | |
| 131 | Me | Cl | Me | Me | H | 2 | T2 | OMe | |
| 132 | Me | Cl | Me | Me | H | 2 | T2 | SMe | |
| 133 | Me | Br | Me | Me | H | 2 | T2 | H | |
| 134 | Me | Br | Me | Me | SO₂-Pr-n | 2 | T2 | H | 124-142 |

TABLE 1-continued

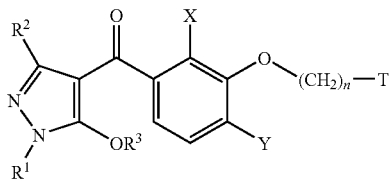

| Compound No. | X | Y | R¹ | R² | R³ | n | T | R⁴ | mp (° C.) or $n_D$ (° C.) |
|---|---|---|---|---|---|---|---|---|---|
| 135 | Me | Br | Me | Me | SO₂-Ph-4-Me | 2 | T2 | H | |
| 136 | Me | Br | Me | Me | CH₂C(=O)Ph | 2 | T2 | H | |
| 137 | Me | Br | Me | Et | H | 2 | T2 | H | |
| 138 | Me | Br | Me | cyclo-Pr | H | 2 | T2 | H | 1.5818(24) |
| 139 | Me | Br | Et | Me | H | 2 | T2 | H | 119-122 |
| 140 | Me | Br | Et | Et | H | 2 | T2 | H | |
| 141 | Me | Br | Et | cyclo-Pr | H | 2 | T2 | H | |
| 142 | Me | Br | Me | Me | H | 2 | T2 | Me | 143-147 |
| 143 | Me | Br | Me | Me | Me | 2 | T2 | Me | |
| 144 | Me | Br | Me | Me | allyl | 2 | T2 | Me | |
| 145 | Me | Br | Me | Me | propargyl | 2 | T2 | Me | |
| 146 | Me | Br | Me | Me | benzyl | 2 | T2 | Me | |
| 147 | Me | Br | Me | Me | SO₂-Me | 2 | T2 | Me | |
| 148 | Me | Br | Me | Me | SO₂-Pr-n | 2 | T2 | Me | |
| 149 | Me | Br | Me | Me | SO₂-Ph-4-Me | 2 | T2 | Me | |
| 150 | Me | Br | Me | Me | CH₂C(=O)Ph | 2 | T2 | Me | |
| 151 | Me | Br | Me | Me | C(=O)Me | 2 | T2 | Me | |
| 152 | Me | Br | Me | Me | C(=O)Ph | 2 | T2 | Me | |
| 153 | Me | Br | Me | Et | H | 2 | T2 | Me | |
| 154 | Me | Br | Me | cyclo-Pr | H | 2 | T2 | Me | 1.5772(24) |
| 155 | Me | Br | Et | Me | H | 2 | T2 | Me | 1.5705(24) |
| 156 | Me | Br | Et | Et | H | 2 | T2 | Me | |
| 157 | Me | Br | Et | cyclo-Pr | H | 2 | T2 | Me | |
| 158 | Me | Br | Me | Me | H | 2 | T2 | Et | 147-156 |
| 159 | Me | Br | Me | Me | H | 2 | T2 | OMe | |
| 160 | Me | Br | Me | Me | H | 2 | T2 | SMe | |
| 161 | Me | Br | Me | cyclo-Pr | H | 2 | T2 | Et | 1.5602(24) |

Reference Example 1

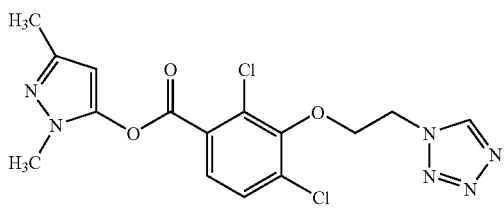

2,4-Dichloro-3-[2-(1H-tetrazol-1-yl)ethoxy]benzoyl chloride (0.60 g) was dissolved in tetrahydrofuran (5 ml), this solution was added dropwise to a tetrahydrofuran (5 ml) solution of 1,3-dimethyl-5-hydroxypyrazole (0.22 g) and triethylamine (0.23 g) at 5° C. and the mixture was stirred at room temperature for 6 hours. After the reaction, the mixture was extracted with ethyl acetate (100 ml) and then washed with diluted hydrochloric acid and an aqueous sodium bicarbonate solution and dried over anhydrous magnesium sulfate. Ethyl acetate was distilled off to obtain the desired 5-{2,4-dichloro-3-[2-(1H-tetrazol-1-yl)ethyloxy]-benzoyloxy}-1,3-dimethylpyrazole (0.65 g).

mp: 138-140° C.

Reference Example 2

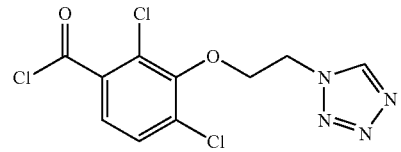

2,4-dichloro-3-[2-(1H-tetrazol-1-yl)ethoxy]benzoic acid (0.46 g) and thionyl chloride (0.36 g) were added in 1,2-dichloroethane (10 ml), two drops of DMF were added and the mixture was refluxed by heating for 3 hours. After cooling, the solvent was distilled off to obtain the desired 2,4-dichloro-3-[2-(1H-tetrazol-1-yl)ethoxy]benzoyl chloride (0.49 g).

mp: 69-73° C.

Reference Example 3

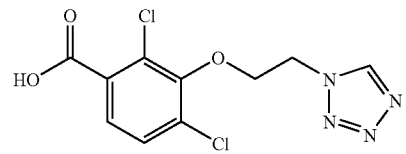

To a methanol (15 ml) solution of ethyl 2,4-dichloro-3-[2-(1H-tetrazol-1-yl)ethoxy]benzoate (0.88 g) were added sodium hydroxide (0.16 g) and water (5 ml), and the mixture was stirred at room temperature for 7 hours. After the addition of water (20 ml) and concentration at reduced pressure, an aqueous sodium hydroxide solution was added and the mixture was washed with ethyl acetate (50 ml). The aqueous layer was acidified with hydrochloric acid and extracted with ethyl acetate. The organic layer was washed with saturated brine and dried over anhydrous magnesium sulfate. Ethyl acetate was distilled off to obtain the desired 2,4-dichloro-3-[2-(1H-tetrazol-1-yl)ethyloxy]-benzoic acid (0.69 g).

mp: 145-146° C.

Reference Example 4

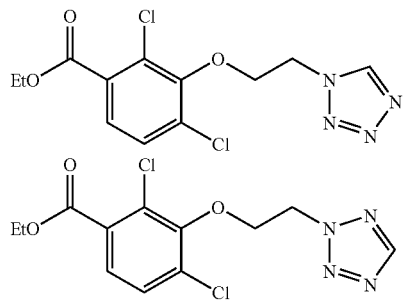

1H-tetrazol (0.45 g) and ethyl 3-(2-bromoethoxy)-2,4-dichlorobenzoate (2.00 g) were suspended in DMF (15 ml), potassium carbonate (1.21 g) and sodium iodide (0.04 g) were added thereto and the mixture was stirred at 80° C. for 3 hours. After the reaction, cool water was added, extracted with ethyl acetate (100 ml) and dried over anhydrous magnesium sulfate. The residue obtained by distilling off ethyl acetate was purified with silica gel column chromatography (elution solvent; ethyl acetate: hexane=1:1) to obtain the desired ethyl 2,4-dichloro-3-[2-(1H-tetrazol-1-yl)ethoxy]benzoate (0.88 g) and ethyl 2,4-dichloro-3-[2-(1H-tetrazol-2-yl)ethoxy]benzoate (0.99 g).

Ethyl 2,4-dichloro-3-[2-(1H-tetrazol-1-yl)ethoxy]-benzoate; $n^D_{20}$=1.5535.

Ethyl 2,4-dichloro-3-[2-(1H-tetrazol-2-yl)ethoxy]-benzoate; $n^D_{20}$=1.5483.

Biological Test Examples

Comparative Compound

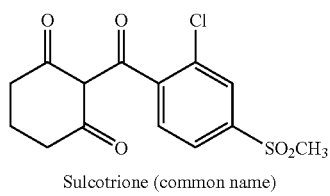

C-1

Sulcotrione (common name)

Test Example 1

Test for herbicidal efficacy against field weeds (Pre-emergence soil spray treatment) Preparation of formulation of the active compound Carrier: DMF 5 parts by weight
Emulsifier: Benzyloxy polyglycol ether 1 part by weight A suitable formulation of an active compound is obtained as an emulsifiable concentrate by mixing 1 part by weight of the active compound with the stated amounts of the carrier and emulsifier. A prescribed amount of the formulation is diluted with water.

In a green house, the seeds of field weeds (*Amaranthus lividus* and *Setaria viridis*) were inoculated by one species per pot on the surface layer in 16 cm² pots filled with field soil (sand loam) and covered with soil. Immediately after the inoculation, the prescribed and diluted solutions of the formulations of respective active compounds prepared according to the above preparation method, were sprayed to the soil. After 2 weeks from the treatment, the herbicidal efficacy of respective active compounds was examined. The evaluation of the herbicidal efficacy was carried out by rating complete death as 100% and as 0% in case of no herbicidal efficacy. In case of showing herbicidal efficacy of 80% or more, such active compounds are evaluated to be practical as herbicides. As typical examples, the study results with Compound Nos. 19 and 96 and those with Comparative compound C-1 are shown in Table 2 below.

TABLE 2

| Pre-emergence soil spray treatment | | | |
|---|---|---|---|
| Compound No. | Amount of drug (g ai/ha) | *Setaria viridis* | *Amaranthus lividus* |
| 19 | 500 | 80 | 90 |
| 96 | 500 | 90 | 80 |
| C-1 | 500 | 30 | 70 |

Note:
ai = active ingredient

Test Example 2

Test for herbicidal efficacy against field weeds (After-emerge stalk and leave spray treatment)

In a green house, young plants (in 2- to 3-leafstages) of field weeds (*Setaria viridis*) were transplanted to 16 cm² pots filled with field soil (sand loam) and the prescribed and diluted solutions of the formulations of respective active compounds, prepared according to the Test Example 1 above were sprayed from the upside of the plants. After 2 weeks from the treatment, the herbicidal efficacy of respective active compounds was examined. The evaluation of the herbicidal efficacy was carried out in the same manner as in Test Example 1 mentioned above. As typical examples, the study results with Compound Nos. 19 and 96 and Comparative compound C-1 are shown in Table 3 below.

TABLE 3

| After-emergence stalk and leaf spray treatment | | |
|---|---|---|
| Compound No. | Amount of drug (g ai/ha) | *Setaria viridis* |
| 19 | 500 | 90 |
| 96 | 500 | 90 |
| C-1 | 500 | 40 |

Test Example 3

Test for selective herbicidal efficacy against field crops (Pre-emergence soil spray treatment)

In a green house, seeds of field crops [*Zea mays* (maize) and *Glycine max* (soy beans)] and field weeds (*Echinochloa crus-galli*, *Digitaria ciliaris*, *Amaranthus lividus* and *Che-* nopodium album) were inoculated on the surface layer in 16 cm² pots filled with field soil (sand loam) and covered with soil. After one day, the prescribed and diluted solutions of the formulations of the active compound, prepared according to the Test Example 1 above were sprayed to the soil. After 2 weeks from the treatment, phytotoxicity to the crops and herbicidal efficacy of the active compound were examined. The evaluation of the herbicidal efficacy and crop phytotoxicity was carried out by rating complete death as 100% and as 0% in case of no herbicidal efficacy and no crop phytotoxicity. In case of showing herbicidal efficacy of 80% or more, such active compounds are evaluated to be practical as herbicides and in case of showing phytotoxicity of 20% or less, such active compounds are evaluated as being superior in safety as herbicides. As typical examples, the study results with Compound No. 12 are shown in Table 4 below.

TABLE 4

Pre-emerge soil spray treatment

| Compound No. | Amount of drug (g ai/ha) | Maize | Soy beans |
|---|---|---|---|
| 12 | 320 | 0 | 10 |

| Compound No. | Echinochloa crus-galli | Digitaria ciliaris | Amaranthus lividus | Chenopodium album |
|---|---|---|---|---|
| 12 | 80 | 80 | 85 | 95 |

Formulation Examples

Formulation Example 1

Granules

To a mixture of Compound No. 14 (10 parts) of the present invention, bentonite (montmorillonite) (30 parts), talc (58 parts) and ligninsulfonate (2 parts) is added water (25 parts), and the mixture is well kneaded, made in granules of 10-40 mesh by an extrusion granulater, which are dried at 40-50° C. to obtain granules.

Formulation Example 2

Granules

Clay mineral particles (95 parts) having particle size distribution of 0.2-2 mm are charged in a rotary mixer, Compound No. 14 (5 parts) of the present invention was sprayed together with a liquid diluent under rotation, wetted uniformly and then dried at 40-50° C. to obtain granules.

Formulation Example 3

Emulsifiable Concentrate

Compound No. 103 (30 parts) of the present invention, xylene (55 parts), polyoxyethylene alkylphenyl ether (8 parts) and calcium alkylbenzene sulfonate (7 parts) were mixed by stirring to obtain emulsions.

Formulation Example 4

Wettable Powder

Compound No. 154 (15 parts) of the present invention, a mixture of white carbon (hydrous amorphous silicon oxide fine powder) and powder clay (1:5) (80 parts), sodium alkylbenzene sulfonate (2 parts) and a polymer (3 parts) of sodium alkylnaphthalene sulfonate formalin polymer were mixed in powder form and made into to wettable powders.

Formulation Example 5

Water-Dispersible Granules

Compound No. 104 (20 parts) of the present invention, sodium ligninsulfonate (30 parts), bentonite (15 parts) and calcined diatomaceous earth powder (35 parts) are well mixed, water was added thereto and the mixture was extruded with a screen of 0.3 mm and dried to obtain water-dispersible granules.

The invention claimed is:

1. Benzoylpyrazoles represented by the formula (I):

(I)

wherein
$R^1$ represents alkyl;
$R^2$ represents alkyl or cycloalkyl;
$R^3$ represents hydrogen, alkyl, alkenyl, alkynyl, aralkyl, alkylsulfonyl, optionally substituted phenylsulfonyl, acyl or acylalkyl;
X represents halogen or alkyl;
Y represents halogen;
n represents 2 or 3, and
T represents a group T1:

(T1)

or a group T2:

(T2)

wherein $R^4$ represents hydrogen, alkyl, alkoxy or alkylthio.

2. The compound according to claim 1, wherein
$R^1$ represents $C_{1-6}$ alkyl;
$R^2$ represents $C_{1-6}$ alkyl or $C_{3-7}$-cycloalkyl;
$R^3$ represents hydrogen, $C_{1-6}$ alkyl, $C_{3-7}$ alkenyl, $C_{3-7}$ alkynyl, $C_{7-12}$ aralkyl, $C_{1-6}$ alkylsulfonyl, optionally $C_{1-6}$ alkyl-substituted phenylsulfonyl, $C_{1-6}$ alkylcarbonyl, benzoyl or benzoyl-$C_{1-6}$ alkyl;
X represents halogen or $C_{1-6}$ alkyl;
Y represents halogen;
n represents 2 or 3; and T represents a group T1:

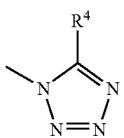

or a group T2:

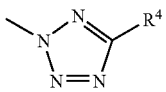

wherein R⁴ represents hydrogen, $C_{1-6}$ alkyl, $C_{1-6}$ alkoxy or $C_{1-6}$ alkylthio.

3. The compound according to claim 1, wherein
R¹ represents methyl or ethyl;
R² represents methyl, ethyl or cyclopropyl;
R³ represents hydrogen, methyl, allyl, propargyl, benzyl, methanesulfonyl, n-propanesulfonyl, optionally methyl-substituted phenylsulfonyl, acyl, benzoyl or phenacyl;
X represents chlorine, bromine or methyl;
Y represents chlorine or bromine;
n represents 2 or 3; and
T represents a group T1:

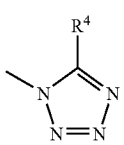

or a group T2:

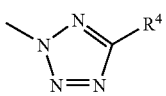

wherein R⁴ represents hydrogen, methyl, ethyl, methoxy or methylthio.

4. A herbicide comprising, as an effective ingredient, the compound according to claim 1.

5. The compound represented by the formula (II):

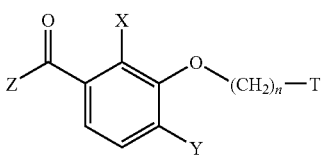

Wherein
X represents halogen or alkyl;
Y represents halogen;
n represents 2 or 3, and
T represents a group T1:

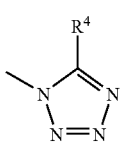

or a group T2:

wherein R⁴ represents hydrogen, alkyl, alkoxy or alkylthio, and Z represents a group:

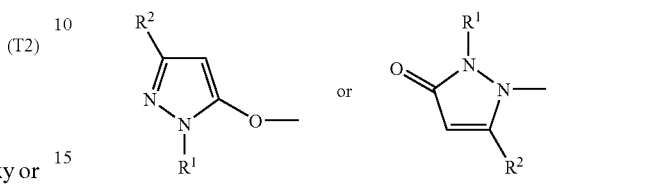

Wherein R¹ represents alkyl;
R² represents alkyl or cycloalkyl.

6. A herbicide comprising, as an effective ingredient, the compound according to claim 2.

7. A herbicide comprising, as an effective ingredient, the compound according to claim 3.

8. A method for preparing a compound of claim 1, comprising using a compound of formula II

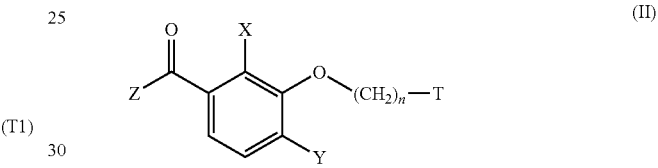

wherein
X represents halogen or alkyl;
Y represents halogen;
n represents 2 or 3, and
T represents a group T1:

or a group T2:

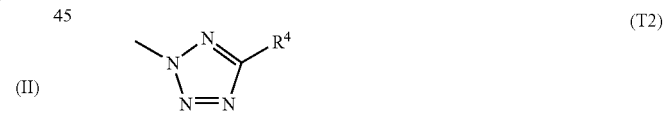

wherein R⁴ represents hydrogen, alkyl, alkoxy or alkylthio and Z represents a group:

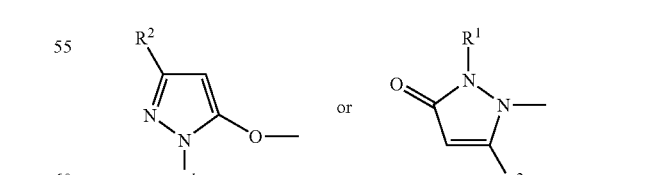

wherein
R¹ represents alkyl;
R² represents alkyl or cycloalkyl, as an intermediate in said method.

* * * * *